(12) United States Patent
Stefan et al.

(10) Patent No.: US 10,307,178 B2
(45) Date of Patent: Jun. 4, 2019

(54) MEDICAL INSTRUMENT

(71) Applicant: Karl Storz SE & Co. KG, Tuttlingen (DE)

(72) Inventors: Jochen Stefan, Wald (DE); Daniel Kärcher, Radolfzell (DE)

(73) Assignee: Karl Storz SE & Co. KG, Tuttlingen (DE)

( * ) Notice: Subject to any disclaimer, the term of this patent is extended or adjusted under 35 U.S.C. 154(b) by 218 days.

(21) Appl. No.: 15/360,408

(22) Filed: Nov. 23, 2016

(65) Prior Publication Data
US 2017/0150982 A1    Jun. 1, 2017

(30) Foreign Application Priority Data
Dec. 1, 2015 (DE) ........................ 10 2015 015 655

(51) Int. Cl.
*A61B 17/00* (2006.01)
*A61B 17/28* (2006.01)
(Continued)

(52) U.S. Cl.
CPC ........ *A61B 17/282* (2013.01); *A61B 17/2812* (2013.01); *A61B 17/2841* (2013.01);
(Continued)

(58) Field of Classification Search
CPC .............. A61B 17/282; A61B 17/2841; A61B 17/2812; A61B 17/29; A61B 2017/00371;
(Continued)

(56) References Cited

U.S. PATENT DOCUMENTS

| | | | | |
|---|---|---|---|---|
| 5,330,502 A | * | 7/1994 | Hassler | A61B 17/29 600/564 |
| 5,354,311 A | * | 10/1994 | Karabin | A61B 17/29 600/564 |

(Continued)

FOREIGN PATENT DOCUMENTS

| | | |
|---|---|---|
| DE | 10036108 A1 | 11/2001 |
| DE | 10314828 B3 | 7/2004 |

(Continued)

OTHER PUBLICATIONS

German Search Report Application No. DE 10 2015 015 6551 Completed: Oct. 6, 2016 8 pages.

(Continued)

*Primary Examiner* — Amy R Weisberg
(74) *Attorney, Agent, or Firm* — Whitmyer IP Group LLC

(57) ABSTRACT

A medical instrument with a hollow shaft, at the proximal end of which a handle is arranged, and at the distal end of which a tool is arranged with a stationary jaw part and with a jaw part that is pivotable relative to the stationary jaw part, a distal end region of the shaft that carries the tool being designed as a tool tip that can be positioned at an angle with respect to the longitudinal axis of the shaft, and the tool being rotatable about the longitudinal axis of the shaft respectively about the longitudinal axis of the tool tip. The axially displaceable actuation element for actuating the pivotable jaw part of the tool are coupled to each other in such a way that, on the one hand, when the axially displaceable actuation element for positioning the tool tip at an angle is actuated, the axially displaceable actuation element for actuating the pivotable jaw part of the tool is necessarily movable at the same time in the axial direction, and, on the other hand, the axially displaceable actuation element for actuating the pivotable jaw part of the tool can be actuated (Continued)

independently of the axially displaceable actuation element for positioning the tool tip at an angle.

11 Claims, 6 Drawing Sheets

(51) Int. Cl.
*A61B 17/29* (2006.01)
*F16D 3/18* (2006.01)

(52) U.S. Cl.
CPC .............. *A61B 17/29* (2013.01); *F16D 3/18* (2013.01); *A61B 2017/00371* (2013.01); *A61B 2017/2902* (2013.01); *A61B 2017/2927* (2013.01); *A61B 2017/2929* (2013.01); *A61B 2017/2936* (2013.01)

(58) Field of Classification Search
CPC .... A61B 2017/2936; A61B 2017/2929; A61B 2017/2927; A61B 2017/2902; F16D 3/18
See application file for complete search history.

(56) References Cited

U.S. PATENT DOCUMENTS

| | | | | |
|---|---|---|---|---|
| 5,456,684 A | * | 10/1995 | Schmidt | A61B 17/29 604/35 |
| 5,609,601 A | * | 3/1997 | Kolesa | A61B 17/29 606/170 |
| 6,913,613 B2 | * | 7/2005 | Schwarz | A61B 17/2909 606/206 |
| 7,087,071 B2 | * | 8/2006 | Nicholas | A61B 17/0218 600/104 |
| 7,241,288 B2 | * | 7/2007 | Braun | A61B 17/29 606/1 |
| 7,476,237 B2 | * | 1/2009 | Taniguchi | A61B 17/29 606/205 |
| 9,757,102 B2 | * | 9/2017 | Bacher | A61B 17/29 |
| 10,117,651 B2 | * | 11/2018 | Whitman | A61B 17/068 |
| 2003/0065358 A1 | * | 4/2003 | Frecker | A61B 17/29 606/205 |
| 2005/0043582 A1 | * | 2/2005 | Stokes | A61B 17/0469 600/101 |
| 2007/0023477 A1 | * | 2/2007 | Whitman | A61B 17/07207 227/175.1 |
| 2009/0088770 A1 | * | 4/2009 | Lim | A61B 17/1615 606/104 |
| 2009/0182193 A1 | * | 7/2009 | Whitman | A61B 1/00101 600/104 |
| 2009/0198272 A1 | * | 8/2009 | Kerver | A61B 17/29 606/205 |
| 2009/0299143 A1 | * | 12/2009 | Conlon | A61B 17/29 600/153 |
| 2012/0259319 A1 | * | 10/2012 | Stefan | A61B 17/29 606/1 |
| 2012/0259358 A1 | * | 10/2012 | Kaercher | A61B 17/29 606/205 |
| 2013/0304083 A1 | * | 11/2013 | Kaercher | A61B 17/00 606/130 |
| 2015/0173786 A1 | * | 6/2015 | Frings | A61B 17/282 606/207 |
| 2015/0238211 A1 | * | 8/2015 | Karcher | A61B 17/00234 606/206 |
| 2015/0374360 A1 | * | 12/2015 | Scheib | A61B 17/068 227/175.1 |

FOREIGN PATENT DOCUMENTS

| | | |
|---|---|---|
| DE | 102014117393 A1 | 6/2015 |
| EP | 0630614 A1 | 12/1994 |
| EP | 2653110 A1 | 10/2013 |
| EP | 2910202 A1 | 8/2015 |

OTHER PUBLICATIONS

European Search Report Application No. 16002431.1 Completed Date: Apr. 4, 2017; dated Apr. 11, 2017 10 Pages.

* cited by examiner

MEDICAL INSTRUMENT

TECHNICAL FIELD

The invention relates to a medical instrument with a hollow shaft, at the proximal end of which a handle is arranged, and at the distal end of which a tool is arranged with a stationary jaw part and with a jaw part that is pivotable relative to the stationary jaw part, a distal end region of the shaft that carries the tool being designed as a tool tip that can be positioned at an angle with respect to the longitudinal axis of the shaft, and the tool being rotatable about the longitudinal axis of the shaft respectively about the longitudinal axis of the tool tip, the rotation of the tool about the longitudinal axis of the shaft being effected via an actuation rod which is mounted rotatably in the hollow shaft and which is operatively connected at its proximal end to the handle, the tool tip being positioned at an angle via an actuation element which is mounted axially displaceably in the hollow shaft and which is operatively connected at its proximal end to the handle, and the pivotable jaw part of the tool being adjustable between a closed position and an open position via an actuation element which is mounted axially displaceably in the hollow shaft and which is operatively connected at its proximal end to the handle.

BACKGROUND

Medical instruments for endoscopic surgery generally have a hollow shaft, at the proximal end of which a handle is arranged, and at the distal end of which a tool is arranged that is composed of two jaw parts movable relative to each other. The tool, designed as a gripping, holding and/or cutting instrument, can be actuated via the handle. To be able to provide the greatest possible range of action within the often confined working conditions in which the tool is used, many endoscopic instruments are designed such that the tool can be angled with respect to the longitudinal axis of the shaft and also such that the tool is rotatable about the longitudinal axis of the shaft.

A problem presented by the medical instruments known from the prior art, with these numerous possible adjustments of the tool tip and/or of the distal tool, is that the angled positioning of the tool tip relative to the proximal shaft region results in a forced movement of the jaw parts relative to each other and/or a rotation movement of the tool tip. To deal with this forced movement, various elaborate compensation mechanisms are known in practice. Although these compensation mechanisms ensure that the tool tip can be angled in a manner substantially free from forced movement, the structure is very complex and runs counter to the compact configuration that is required particularly in endoscopic instruments.

A medical instrument of the type in question is known, for example, from DE 103 14 823 B3. In this known surgical instrument, a movement compensation element is provided which ensures that a rotation caused by the angled positioning of the tool tip is compensated.

SUMMARY

Proceeding from this, it is the object of the invention to configure a medical instrument of the aforementioned type mentioned which, while having a compact configuration, ensures that the tool tip can be angled in a manner substantially free from forced movement.

According to the invention the solution to this problem is characterized in that the axially displaceable actuation element for positioning the tool tip at an angle and the axially displaceable actuation element for actuating the pivotable jaw part of the tool are coupled to each other in such a way that, on the one hand, when the axially displaceable actuation element for positioning the tool tip at an angle is actuated, the axially displaceable actuation element for actuating the pivotable jaw part of the tool is necessarily movable at the same time in the axial direction, and, on the other hand, the axially displaceable actuation element for actuating the pivotable jaw part of the tool can be actuated independently of the axially displaceable actuation element for positioning the tool tip at an angle.

Since, according to the invention, the movements of the axially displaceable actuation element for positioning the tool tip at an angle are coupled with the movements of the axially displaceable actuation element for actuating the pivotable jaw part, the shifting of the stationary jaw part relative to the pivotable jaw part, forced by the angled positioning of the tool tip, is compensated, because the pivotable jaw part is now at the same time actuated to the same extent, and therefore the adopted position of the jaw parts relative to each other is maintained.

In one practical embodiment of the invention, it is further proposed that the axially displaceable actuation element for positioning the tool tip at an angle and the axially displaceable actuation element for actuating the pivotable jaw part of the tool are arranged parallel to each other in the direction of the longitudinal axis of the shaft and are at the same radial distance from the rotation axis about which the tool tip can be positioned at an angle relative to the proximal part of the shaft. The fact that the two actuation elements are at the same distance from the rotation axis ensures that both actuation elements are shifted by the same axial distance during the coupled simultaneous movement.

Moreover, in a preferred embodiment of the invention, it is proposed that the actuation rod for rotating the tool is composed of two parts, namely a distal sub-region mounted in the pivotable tool tip and a sub-region mounted in the proximal part of the shaft, and the two mutually facing end faces of the sub-regions of the actuation rod are in engagement with each other at the transition to the pivotable tool tip via end-face toothing arrangements. The two-part design of the actuation rod, for rotating the tool, and the two end-face toothing arrangements of the two sub-regions of the actuation rod allow the rotation movement to be transmitted with little play from the shaft region to the tool tip.

In order to couple the tool to the distal sub-region of the actuation rod, it is proposed according to the invention that the proximal end of the pivotable jaw part is mounted in the interior of the distal sub-region of the actuation rod rotatable about the longitudinal axis of the shaft, and the distal sub-region of the actuation rod and the proximal end of the pivotable jaw part are connected to each other with force-fit engagement via a driving pin passing radially through the two components such that the driving pin transmits the rotation of the distal sub-region of the actuation rod directly to the pivotable jaw part.

According to one practical embodiment of the invention, it is proposed that the free ends on both sides of the driving pin are mounted in a slide which, decoupled from the rotation of the distal sub-region of the actuation rod, is mounted axially displaceably in the tool tip.

In order to adjust the pivotable jaw part between a closed position and an open position, it is proposed according to the invention that the driving pin is mounted in the slide in such a way that the driving pin is mounted in a circumferential groove of the slide so as to rotate freely about the longitudinal axis of the shaft and is axially displaceable in the direction of the longitudinal axis of the shaft via the slide.

In order to decouple the movement of the pivotable jaw part from the rotation of the tool tip, it is proposed, according to a preferred embodiment of the invention, that the driving pin is mounted in an oblong hole in the distal sub-region of the actuation rod, the axial extent of which oblong hole corresponds to the axial displacement path of the slide.

It is further proposed according to the invention that the axially displaceable actuation element, for actuating the pivotable jaw part of the tool, and the slide are coupled to each other in such a way that an axial displacement of the actuation element causes an axial movement of the slide free from play. The freedom from play of the jaw part actuation is important, since the operator is able to precisely gauge the force that he introduces, and an at all times secure hold between the jaw parts of the tool is ensured.

Finally, it is proposed according to the invention that the tooth flanks of the individual teeth of the two end-face toothing arrangements are designed tapering radially outward. By virtue of this design of the tooth flanks of the individual teeth of the two end-face toothing arrangements, it is possible, without axial compensation, to prevent the teeth on both sides of the end-face toothing arrangements from jamming during a pivoting movement of the end-face toothing arrangements relative to each other.

BRIEF DESCRIPTION OF THE DRAWINGS

Further features and advantages of the invention will become clear from the attached drawings in which an illustrative embodiment of a medical instrument according to the invention is shown simply by way of example, without limiting the invention to this illustrative embodiment. In the drawings.

DETAILED DESCRIPTION

Figure 1:
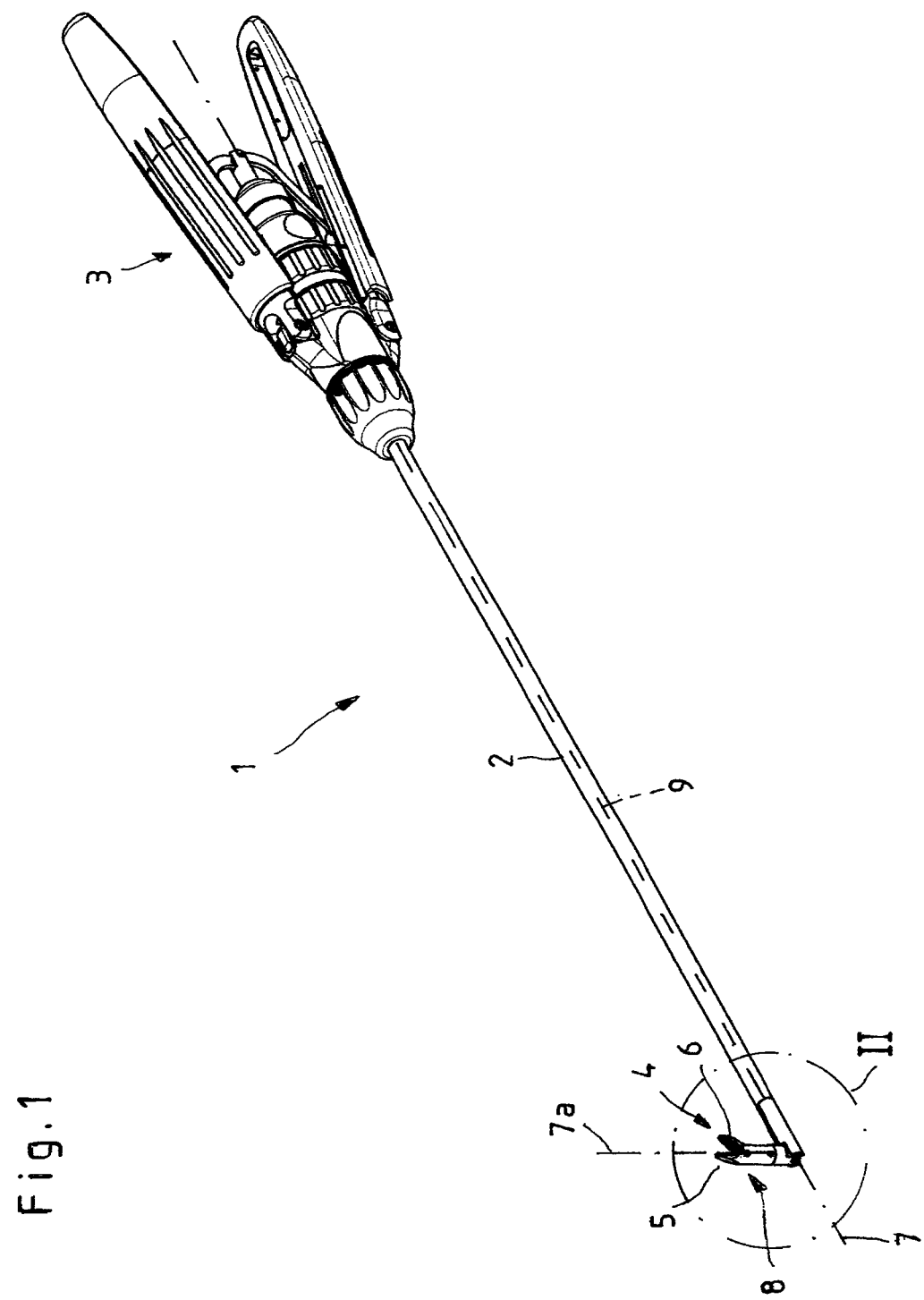
FIG. 1 shows a perspective side view of a medical instrument according to the invention.

FIG. 1 shows a medical instrument 1 with a hollow shaft 2, at the proximal end of which a handle 3 is arranged, and at the distal end of which a tool 4 is arranged that is composed of a stationary jaw part 5 and of a jaw part 6 pivotable with respect to the stationary jaw part 5.

To give the tool 4 the greatest number of possible degrees of freedom of movement relative to the shaft 2, a distal end region of the shaft 2 that carries the tool 4 is designed as a tool tip 8 that can be positioned at an angle with respect to the longitudinal axis 7 of the shaft 2. In the view according to FIG. 1, the tool tip 8 is angled at approximately 90° with respect to the longitudinal axis 7 of the shaft 2.

Moreover, the tool 4 is rotatable about the longitudinal axis 7 of the shaft 2, respectively about the longitudinal axis 7a of the tool tip 8 when the latter is angled, the rotation of the tool 4 about the longitudinal axis 7 of the shaft 2 being effected via an actuation rod 9 which is mounted rotatably in the hollow shaft 2 and which is operatively connected at its proximal end to the handle 3, and the actuation rod 9 is composed of two parts, namely a distal sub-region 10 mounted in the pivotable tool tip 8 and a sub-region 11 mounted in the proximal part of the shaft 2

To form the actuation rod 9, it is possible to use both a solid rod and also a hollow tube.

Figure 2:
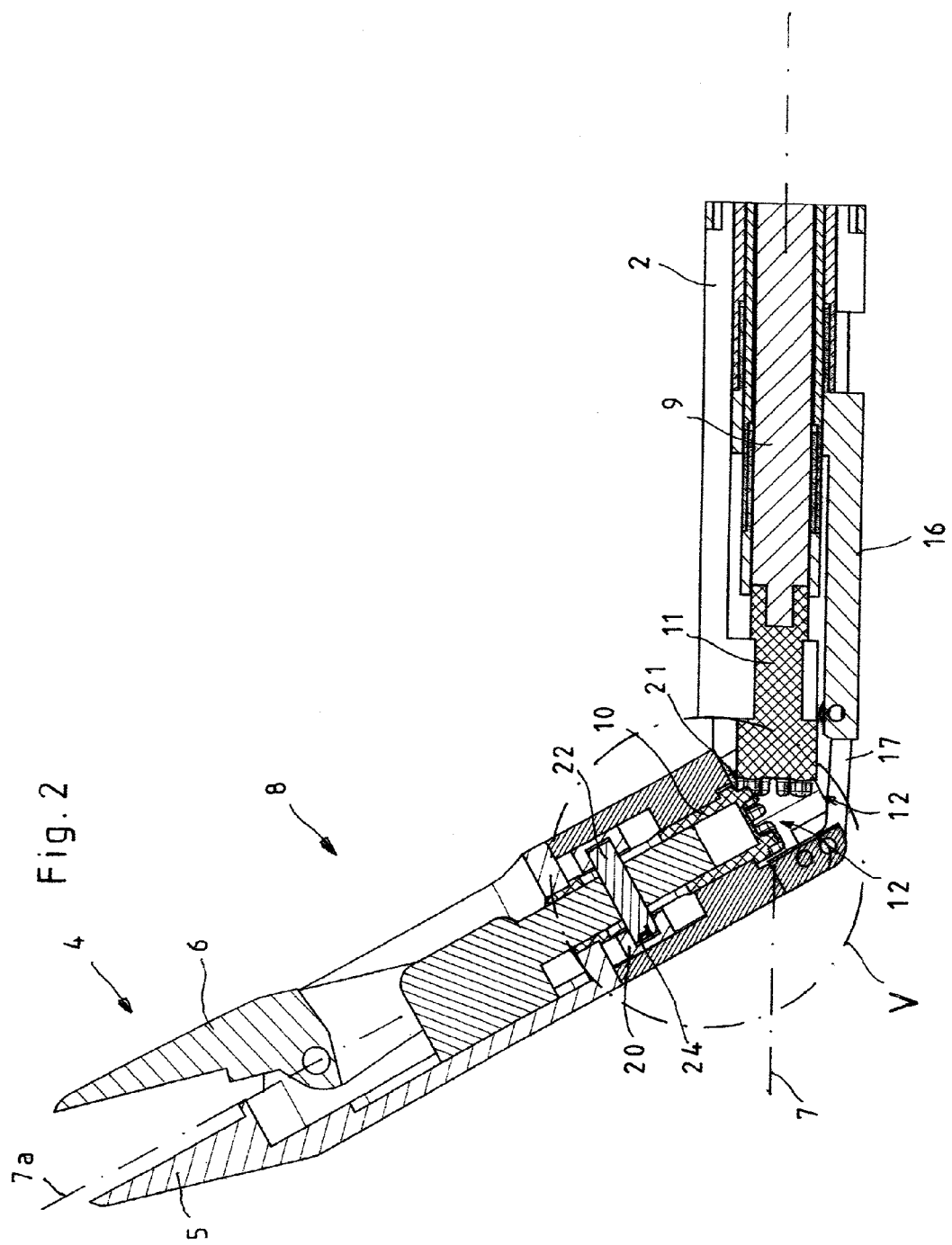
FIG. 2 shows a longitudinal section of the detail II according to FIG. 1, depicting an only partially angled position.

The two mutually facing end faces of the sub-regions 10 and 11 of the actuation rod 9 are in engagement with each other at the transition to the pivotable tool tip 8 via end-face toothing arrangements 12, as can be seen from the schematic cross-sectional view according to FIG. 2. These two end-face toothing arrangements 12 of the two sub-regions 10 and 11 of the actuation rod 9 have the effect that, even in a position in which both sub-regions 10 and 11 of the actuation rod 9 are arranged at an angle relative to each other, the tool 4 is rotatable about the longitudinal axis 7 of the shaft 2. The end-face toothing arrangements 12 transmit the rotation of the proximal sub-region 11 of the actuation rod 9 about the longitudinal axis 7 of the shaft 2 to the distal sub-region 10 of the actuation rod 9.

FIG. 2 shows the set-up of the two end-face toothing arrangements 12 inside the shaft 2 with the aid of a longitudinal section in the area of the transition from the proximal shaft 2 to the angled distal tool tip 8.

A main problem in designing the two end-face toothing arrangements 12 of the mutually pivotable sub-regions 10 and 11 of the actuation rod 9 is to ensure that individual teeth 13 of the end-face toothing arrangements 12 do not jam and block each other during the pivoting movement.

Figure 6:
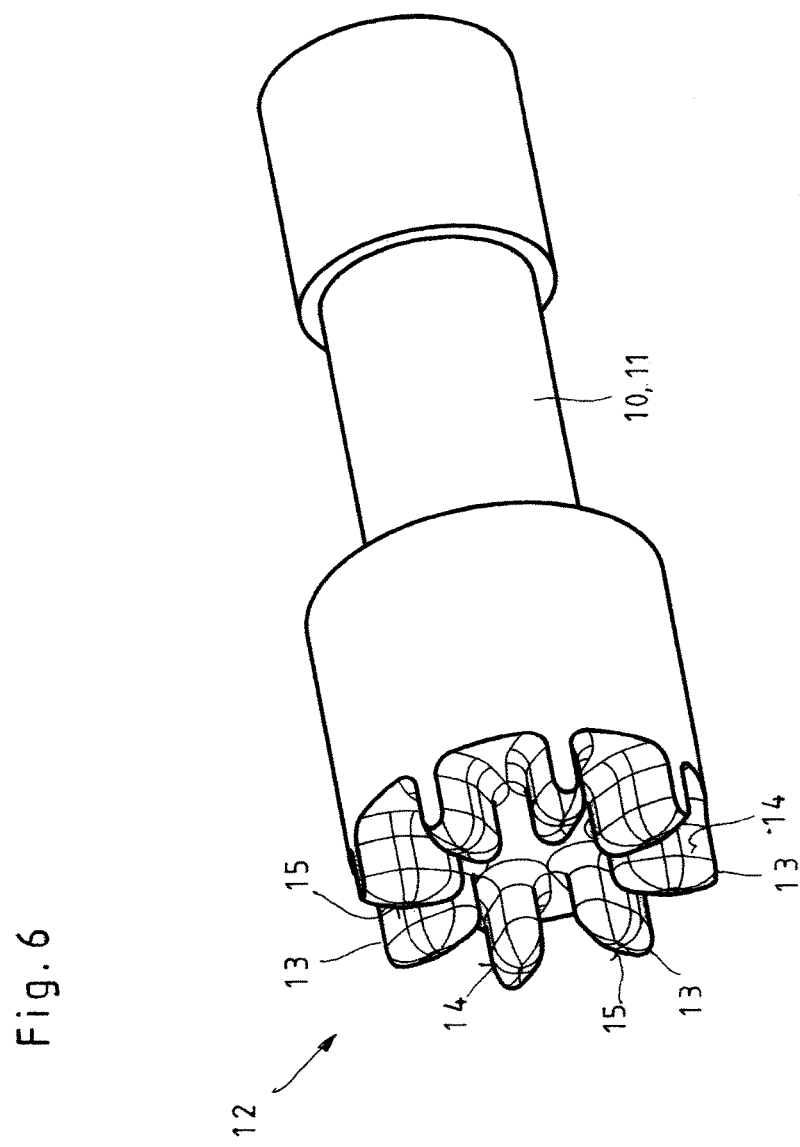
FIG. 6 shows a perspective view of an end-face toothing arrangement according to FIG. 2.

FIG. 6 shows a perspective view of one of the two identically configured end-face toothing arrangements 12. As can be seen from FIG. 6, the tooth flanks 14 of the individual teeth 13 of the two end-face toothing arrangements 12 are designed tapering radially outward. By designing the tooth flanks 14 of the individual teeth 13 of the two end-face toothing arrangements 12 such that they taper radially outward in relation to the respective rotating arrangement 12, the teeth 13 on both sides of the end-face toothing arrangements 12 are also prevented from jamming during a pivoting movement of the end-face toothing arrangements 12 relative to each other. This permanent freedom from jamming makes it possible to do without axial compensation, for example in the form of spring pretensioning. By virtue of the radially outwardly tapering design of the individual teeth 13 of the two end-face toothing arrangements 12, there is always sufficient lateral clearance for the individual teeth 13, specifically in the radially outer area, with respect to the adjacent teeth 13 of the respective other end-face toothing arrangement 12.

In the embodiment of the end-face toothing arrangements 12 shown in the figures, the tooth flanks 14 of the individual teeth 13 of the two end-face toothing arrangements 12 are additionally designed also to taper radially inward, as a result of which the freedom of movement of the individual teeth 13 of the two end-face toothing arrangements 12 relative to each other is further increased.

It will also be seen from the perspective view according to FIG. 6 that the tooth heads 15 of the individual teeth 13 of the two end-face toothing arrangements 12 are rounded. This rounding of the tooth heads 15, which form the top of the individual teeth 13, also makes it easier for the end-face toothing arrangements 12 to be pivoted relative to each other without jamming.

In addition to ensuring that the tool tip 8 pivots without jamming in the area of the end-face toothing arrangements 12, a fundamental problem with a medical instrument 1 according to FIG. 1 is that the angled positioning of the tool tip 8 generally causes a change of position of the jaw parts 5 and 6 of the tool 4 relative to each other. In practice, this means that the jaw parts 5 and 6 of the tool 4 begin to close as the angle of the tool tip 8 increases and, conversely, begin to open as the angle of the tool tip 8 becomes smaller. Such positive coupling of the movements is to be avoided in order to ensure that the operators always has the same action on the tool 4.

As can be seen from FIG. 2, the angled positioning of the tool tip 8 is effected via an actuation element 16 which is mounted axially displaceably in the hollow shaft 2 and which is operatively connected at its proximal end to the handle 3 and is designed as a pull/push rod. The actuation element 16 is connected to the tool tip 8 via an articulated lever 17 which, at the proximal end, is hinged on the actuation element 16 and, at the distal end, is hinged on the tool tip 8.

Figure 3:
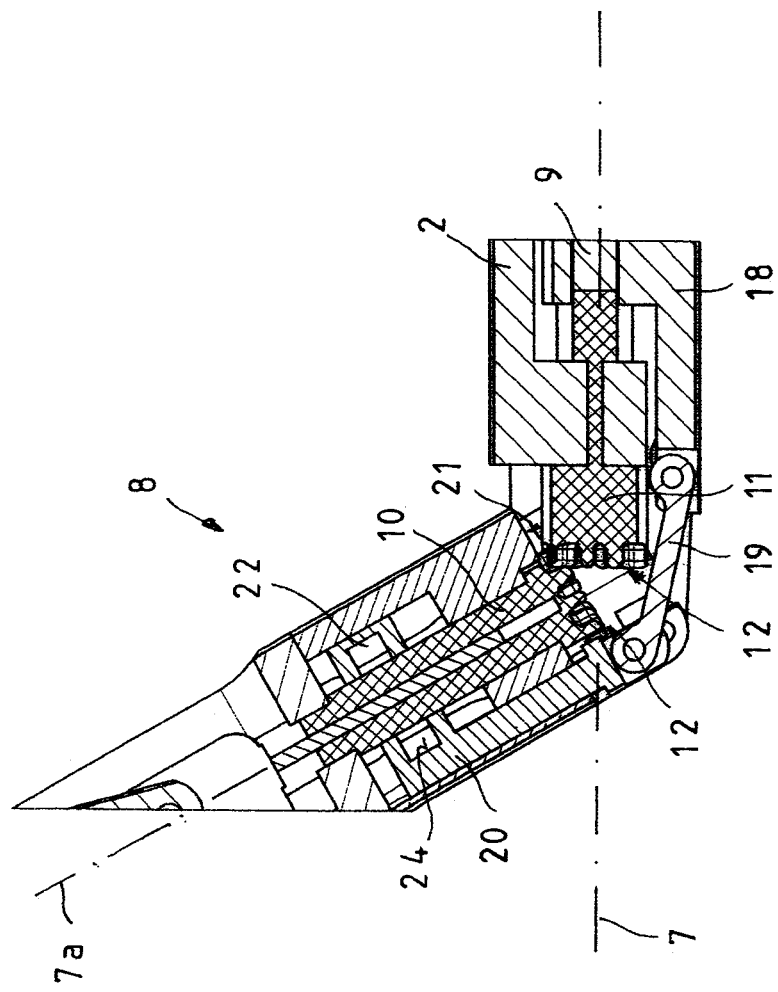
FIG. 3 shows a partial view according to FIG. 2, but depicting the longitudinal section in another vertical plane.

As can be seen from FIG. 3, the adjustment of the pivotable jaw part 6 of the tool 4 between a closed position and an open position is also effected via an actuation element 18 which is mounted axially displaceably in the hollow shaft 2 and which is operatively connected at its proximal end to the handle 3 and is likewise designed as a pull/push rod. The actuation element 18 is connected to the pivotable jaw part 6 via an articulated lever 19 which, at the proximal end, is hinged on the actuation element 18 and, at the distal end, is hinged on a slide 20, which is operatively connected to the pivotable jaw part 6.

To avoid the undesirable forced movement of the tool 4 during the pivoting of the tool tip 8, in the medical instrument 1 shown the axially displaceable actuation element 16 for positioning the tool tip 8 at an angle and the axially displaceable actuation element 18 for actuating the pivotable jaw part 6 of the tool 4 are coupled to each other in such a way that, on the one hand, when the axially displaceable actuation element 16 for positioning the tool tip 8 at an angle is actuated, the axially displaceable actuation element 18 for actuating the pivotable jaw part 6 of the tool 4 is necessarily movable at the same time in the axial direction, and, on the other hand, the axially displaceable actuation element 18 for actuating the pivotable jaw part 6 of the tool 4 can be actuated independently of the axially displaceable actuation element 16 for positioning the tool tip 8 at an angle.

Since the movements of the axially displaceable actuation element 16 for positioning the tool tip 8 at an angle are coupled in this way with the movements of the axially displaceable actuation element 18 for actuating the pivotable jaw part 6 of the tool 4, the shifting of the stationary jaw part 5 relative to the pivotable jaw part 6, forced by the angled positioning of the tool tip 8, is compensated, because the pivotable jaw part 6 is now at the same time actuated to the same extent, and therefore the adopted position of the jaw parts 5 and 6 relative to each other is maintained.

Figure 4:
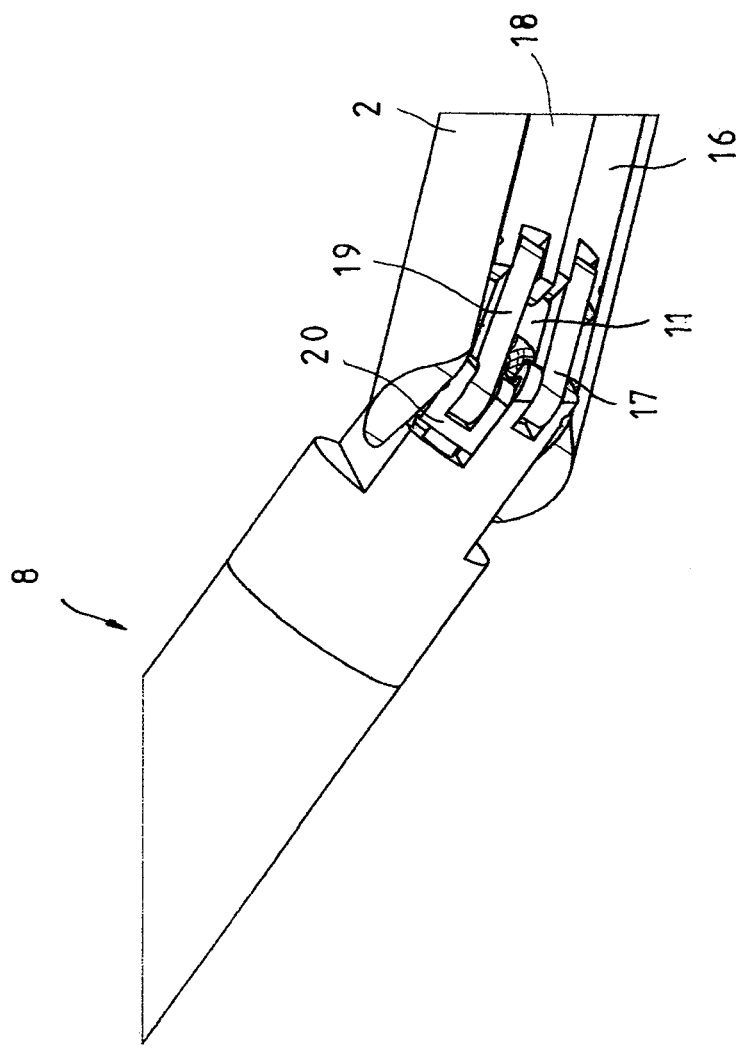
FIG. 4 shows a partial bottom view of the detail II according to FIG. 1.

As can be seen by comparing the bottom view according to FIG. 4 with FIGS. 2 and 3, the axially displaceable actuation element 16 for positioning the tool tip 8 at an angle and the associated articulated lever 17, and the axially displaceable actuation element 18 for actuating the pivotable jaw part 6 of the tool 4 and the associated articulated lever 19, are arranged parallel to each other in the direction of the longitudinal axis 7 of the shaft 2 and are at the same radial distance from the rotation axis 21 about which the tool tip 8 is pivotable relative to the proximal part of the shaft 2.

On account of the parallel arrangement of the axially displaceable actuation element 16 for positioning the tool tip 8 at an angle and the associated articulated lever 17, and of the axially displaceable actuation element 18 for actuating the pivotable jaw part 6 of the tool 4 and the associated articulated lever 19, and on account of the same radial distance from the rotation axis 21, the pivoting movement is coordinated such that the jaw parts 5 and 6 of the tool 4 maintain their position by means of the angle relationship or the arrangement of the actuation elements 16 and 18 and of the articulated levers 17 and 19. The coupling of the actuation elements 16 and 18 and their above-described structurally geometric arrangement with respect to each other synchronize the axial movements of the actuation elements 16 and 18 and, as a result, also the position of the jaw parts 5 and 6 of the tool 4 relative to each other.

The transmission of the movement of the axially displaceable actuation element 18 for actuating the pivotable jaw part 6 of the tool 4, and of the articulated lever 19 coupled to the actuation element 18, to the pivotable jaw part 6 is effected via the slide 20 mounted axially displaceably on the distal sub-region 10 of the actuation rod 9, as will be seen from the comparison of FIGS. 2, 3 and 5 described below.

The proximal end of the pivotable jaw part 6 is mounted in the interior of the distal sub-region 10 of the actuation rod 9 rotatable about the longitudinal axis 7 of the shaft 2. In the area of the slide 20 mounted on the distal sub-region 10 of the actuation rod 9, a driving pin 22 passes through the proximal end of the pivotable jaw part 6 and the distal sub-region 10 of the actuation rod 9, in such a way that the free ends of the driving pin 22 are mounted in the slide 20.

Figure 5:
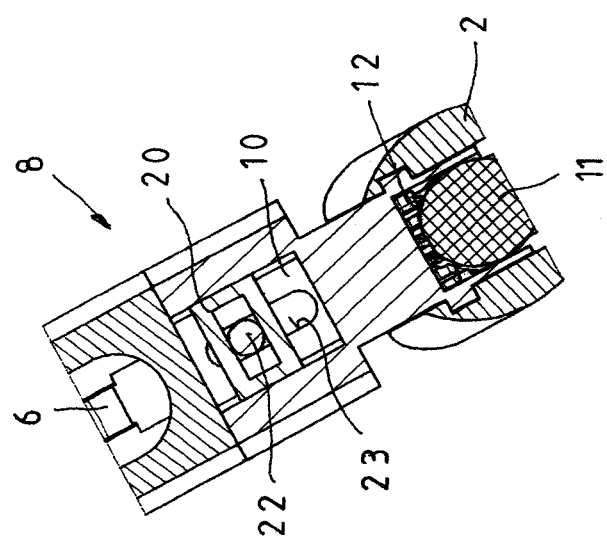
FIG. 5 shows a bottom view of the detail V according to FIG. 2.

As can be seen from the view according to FIG. 5, the driving pin 22 is mounted in an oblong hole 23 in the distal sub-region 10 of the actuation rod 9, the axial extent of which oblong hole 23 corresponds to the axial displacement path of the slide 20.

Thus, by way of the hinged coupling to the articulated lever 19 and to the slide 20, the axial displacement of the actuation element 18 causes an axial displacement of the driving pin 22 inside the oblong hole 23. On account of the force-fit coupling of the driving pin 22 to the proximal end of the pivotable jaw part 6, the pivotable jaw part 6 is adjustable between an open position and a closed position relative to the stationary jaw part 5.

The driving pin 22 passing through the proximal end of the pivotable jaw part 6 and the distal sub-region 10 of the actuation rod 9 connects the two components 10 and 6 to each other with force-fit engagement, such that the driving pin 22 transmits the rotation of the distal sub-region 10 of the actuation rod 9 directly to the pivotable jaw part 6 when the distal sub-region 10 of the actuation rod 9, with interposition of the end-face toothing arrangements 12, is driven in rotation about the longitudinal axis 7 by the sub-region 11 of the actuation rod 9 mounted in the proximal part of the shaft 2.

To ensure that the slide 20 mounted axially displaceably in the tool tip 8 is decoupled from the rotation of the distal sub-region 10 of the actuation rod 9, the driving pin 22 is mounted in a circumferential groove 24 of the slide 20 so as to rotate freely about the longitudinal axis 7 of the shaft 2.

A medical instrument 1 configured as described above is distinguished by the fact that the tool tip 8 can be positioned at an angle in a manner substantially free from forced movement and without compensation elements.

The invention claimed is:

1. A medical instrument, comprising:
a hollow shaft having a proximal end, a distal end, and a longitudinal axis extending therebetween;
a handle arranged at the proximal end of the shaft;
a first actuation element mounted axially displaceably in the shaft and having a proximal end operatively connected to the handle;
a second actuation element mounted axially displaceably in the shaft and having a proximal end operatively connected to the handle;
an actuation rod mounted rotatably in the shaft and having a proximal end operatively connected to the handle;
a tool tip arranged at the distal end of the shaft, the tool tip positionable at an angle relative to a proximal portion of the shaft via the first actuation element, the angle defined between a longitudinal axis of the tool tip and the longitudinal axis of the shaft; and
the tool tip including a tool rotatable about the longitudinal axis of the tool tip via the actuation rod, the tool including a stationary jaw part and a pivotable jaw part that is pivotable relative to the stationary jaw part between a closed position and an open position via the second actuation element;
wherein the second actuation element is independently actuatable relative to the first actuation element; and
wherein the first actuation element and the second actuation element are coupled to each other in such a way that when the first actuation element is actuated the second actuation element is necessarily movable at a same time in a same axial direction.

2. The medical instrument of claim 1, wherein the first actuation element and the second actuation element are arranged parallel to each other in a direction of the longitudinal axis of the shaft; and
wherein the first actuation element and the second actuation element are at a same radial distance from a rotation axis about which the tool tip is positionable at the angle relative to the proximal portion of the shaft.

3. The medical instrument of claim 2, wherein the actuation rod includes a distal sub-region mounted in the tool tip and a proximal sub-region mounted in the proximal portion of the shaft; and
wherein mutually facing end faces of the distal sub-region and the proximal sub-region of the actuation rod are in engagement with each other via end-face toothing arrangements at a transition to the tool tip.

4. The medical instrument of claim 1, wherein the actuation rod includes a distal sub-region mounted in the tool tip and a proximal sub-region mounted in the proximal portion of the shaft; and
wherein mutually facing end faces of the distal sub-region and the proximal sub-region of the actuation rod are in engagement with each other via end-face toothing arrangements at a transition to the tool tip.

5. The medical instrument of claim 4, wherein a proximal end of the pivotable jaw part is mounted in an interior of the distal sub-region of the actuation rod;
wherein the distal sub-region of the actuation rod and the proximal end of the pivotable jaw part are connected to each other with force-fit engagement via a driving pin passing radially through the distal sub-region of the actuation rod and the proximal end of the pivotable jaw part; and
wherein the driving pin transmits rotation of the distal sub-region of the actuation rod directly to the pivotable jaw part.

6. The medical instrument of claim 5, wherein free ends on opposing sides of the driving pin are mounted in a slide; and
wherein the slide is mounted axially displaceably in the tool tip, and is decoupled from rotation of the distal sub-region of the actuation rod.

7. The medical instrument of claim 6, wherein the driving pin is mounted in a circumferential groove of the slide; and
wherein the driving pin is axially displaceable in a direction of the longitudinal axis of the shaft via the slide.

8. The medical instrument of claim 7, wherein the driving pin is mounted in an oblong hole in the distal sub-region of the actuation rod; and
wherein an axial extent of the oblong hole corresponds to an axial displacement path of the slide.

9. The medical instrument of claim 6, wherein the driving pin is mounted in an oblong hole in the distal sub-region of the actuation rod; and
wherein an axial extent of the oblong hole corresponds to an axial displacement path of the slide.

10. The medical instrument of claim 6, wherein the second actuation element and the slide are coupled to each other such that an axial displacement of the second actuation element causes an axial movement of the slide.

11. The medical instrument of claim 4, wherein tooth flanks of individual teeth of the end-face toothing arrangements taper outward radially.

* * * * *